(12) United States Patent
Arai et al.

(10) Patent No.: US 8,114,009 B2
(45) Date of Patent: Feb. 14, 2012

(54) CORONARY ARTERY BYPASS GRAFTING DEVICE

(75) Inventors: Hirokuni Arai, Tokyo (JP); Akira Kawamata, Akita (JP); Hideaki Asai, Akita (JP)

(73) Assignee: Sumitomo Bakelite Company, Ltd., Tokyo (JP)

( * ) Notice: Subject to any disclaimer, the term of this patent is extended or adjusted under 35 U.S.C. 154(b) by 1340 days.

(21) Appl. No.: 11/665,181

(22) PCT Filed: Oct. 6, 2005

(86) PCT No.: PCT/JP2005/018559
§ 371 (c)(1),
(2), (4) Date: Apr. 12, 2007

(87) PCT Pub. No.: WO2006/041014
PCT Pub. Date: Apr. 20, 2006

(65) Prior Publication Data
US 2009/0030270 A1    Jan. 29, 2009

(51) Int. Cl.
*A61B 17/00* (2006.01)
(52) U.S. Cl. ........................................................ 600/37
(58) Field of Classification Search ............ 600/16, 600/37; 128/897–899
See application file for complete search history.

(56) References Cited

U.S. PATENT DOCUMENTS

| | | | |
|---|---|---|---|
| 4,524,805 A * | 6/1985 | Hoffman | 137/846 |
| 5,301,707 A * | 4/1994 | Hofsteenge | 137/12 |
| 5,727,569 A | 3/1998 | Benetti et al. | |
| 5,836,311 A | 11/1998 | Borst et al. | |
| 6,074,375 A | 6/2000 | Stiles | |
| 6,338,712 B2 * | 1/2002 | Spence et al. | 600/201 |
| 6,346,077 B1 | 2/2002 | Taylor et al. | |
| 6,394,951 B1 | 5/2002 | Taylor et al. | |
| 6,447,443 B1 * | 9/2002 | Keogh et al. | 600/37 |
| 6,730,020 B2 * | 5/2004 | Peng et al. | 600/201 |
| 6,740,098 B2 | 5/2004 | Abrams et al. | |
| 7,146,225 B2 * | 12/2006 | Guenst et al. | 607/119 |
| 7,445,594 B1 * | 11/2008 | Borst et al. | 600/37 |
| 7,479,104 B2 * | 1/2009 | Lau et al. | 600/37 |
| 2002/0019580 A1 * | 2/2002 | Lau et al. | 600/37 |
| 2002/0058856 A1 | 5/2002 | Peng et al. | |
| 2003/0060685 A1 * | 3/2003 | Houser et al. | 600/206 |
| 2003/0078471 A1 * | 4/2003 | Foley et al. | 600/37 |

FOREIGN PATENT DOCUMENTS

JP    09-150386    6/1997

(Continued)

OTHER PUBLICATIONS

Taiwan Search Report for Application No. 094135851.

(Continued)

*Primary Examiner* — Charles A Marmor, II
*Assistant Examiner* — Catherine E Burk
(74) *Attorney, Agent, or Firm* — Smith, Gambrell & Russell, LLP

(57) ABSTRACT

A coronary artery bypass grafting device includes a plurality of attachment members each having: a flexible tube (102); a suction cup portion (101) provided in a tip end side of the flexible tube (102); a three-way cock (103) provided in the flexible tube (102); and a holding member (104) that holds the flexible tube (102). At least one of the attachment members further includes a duckbill valve (111) provided in the flexible tube (102).

22 Claims, 7 Drawing Sheets

FOREIGN PATENT DOCUMENTS

| | | |
|---|---|---|
| JP | 2003-529403 | 10/2003 |
| JP | 2004-500917 | 1/2004 |
| JP | 2004-502473 | 1/2004 |
| JP | 2004-121766 | 4/2004 |
| TW | 510788 | 11/2002 |
| WO | 01/17437 | 3/2001 |
| WO | 01/58361 | 8/2001 |
| WO | 01/80755 | 11/2001 |
| WO | 02/054937 | 7/2002 |
| WO | 03/068097 | 8/2003 |

OTHER PUBLICATIONS

Japanese Office Action issued on Jan. 19, 2010 for Japanese Application No. 2006-540911.

* cited by examiner

109

CORONARY ARTERY BYPASS GRAFTING DEVICE

TECHNICAL FIELD

The present invention relates to a coronary artery bypass grafting device.

BACKGROUND ART

In recent years, catheter intervention for patients suffering from an ischemic heart disease such as myocardial infarct has been increasingly widespread. Typical catheter intervention includes percutaneous transluminal coronary angioplasty or intravascular stent placement. These treatments are less invasive and require a short stay in a hospital.

On the other hand, effectiveness of coronary artery bypass grafting (hereinafter referred to as CABG) has been widely recognized for patients who cannot undergo the catheter treatment. This method is intended for anastomosing one end of a bypass blood vessel such as an ablated internal thoracic artery or gastroepiploic artery to a peripheral side of a coronary artery with stenosis that may cause ischemia to eliminate the ischemia.

Patients who undergo the CABG often have a plurality of coronary arteries with obstruction or stenosis, a calcified ascending aorta, a chronic disease of brain, kidney, or a respiratory organ, and are elderly people, and thus the CABG may pose substantial risk to the patients. The highest risk to the patients is to stop the heart and use a heart-lung machine for extracorporeal circulation. Applying the heart-lung machine to patients with advanced arteriosclerosis is like supplying water to a rusty water pipe under high pressure. Thus, accretions in a blood vessel may be swept away to block another blood vessel, thereby causing a complication such as brain infarct and the like.

For such patients, an attempt has been made to anastomose a bypass graft without a heart-lung machine while the heart is beating, and satisfactory results have been achieved. This method is called off-pump coronary artery bypass (hereinafter abbreviated as OPCAB).

The problem of the OPCAB is that performing a complete anastomosis in a short time requires skills because the heart is beating. An imperfect anastomosis may cause a blood clot to form in a coronary artery or a bypass blood vessel from the anastomosis portion to cause obstruction. For this problem, a stabilizer is used to control movement of the anastomosis portion and allow the anastomosis of the bypass blood vessel in a stable manner, thereby increasing accuracy of the anastomosis and significantly increasing the results of the OPCAB (Patent Document 1).

Further, in order to increase accuracy of an anastomosis of an affected area that is difficult to anastomose because the area cannot be seen from the front in a normal state, a device is disclosed that is attached to and holds the heart to adjust the position of the heart (Patent Document 2). The device disclosed in Patent Document 2 includes one suction cup portion attachable to a heart wall surface, one arm for adjusting the position of the suction cup portion, and a suction tube that communicates with the suction cup portion and is connectable to a suction source. This device, however, adjusts the position of the heart by a force from one direction, which may cause displacement or fall of the heart during the anastomosis with the position of the heart being adjusted.

[Patent Document 1] U.S. Pat. No. 5,836,311
[Patent Document 2] International Publication No. 02/054937

DISCLOSURE OF THE INVENTION

The present invention is achieved in view of the above described circumstances, and provides a coronary artery bypass grafting device that can adjust the position of the heart with little displacement or fall of the heart and perform an anastomosis with safety in an affected area that is difficult to anastomose in off-pump coronary artery bypass.

According to the present invention, there is provided a coronary artery bypass grafting device comprising a plurality of attachment members each including: a flexible tube; a suction cup portion provided in a tip end side of the flexible tube; a switching (an opening and closing) member provided in the flexible tube; and a holding member that holds the flexible tube, at least one of the attachment members further including a check valve provided in the flexible tube.

The coronary artery bypass grafting device according to the present invention is a device for holding a subject to be attached, specifically, the heart in a predetermined position. The coronary artery bypass grafting device according to the present invention includes the plurality of attachment members, and at least one of the attachment members includes the check valve. The plurality of attachment members each has the suction cup portion. Thus, the coronary artery bypass grafting device according to the present invention includes a plurality of suction cup portions. This allows the subject to be attached, specifically, the heart to be held at a plurality of positions. This allows the heart to be held in the predetermined position in a stable manner. At least one of the attachment members includes the check valve, and thus even if a suction cup portion in one of the attachment member is detached from the heart, as for the other suction cup portion attached on the heart, the vacuum breakdown is prevented and the negative pressure is kept therein, keeping the suction cup portion attached to the heart. This allows an anastomosis procedure in coronary artery bypass grafting to be performed in a stable manner.

According to the present invention, there is provided a coronary artery bypass grafting device comprising a plurality of attachment members each including: a flexible tube; a suction cup portion provided in a tip end side of the flexible tube; a switching (an opening and closing) member provided in the flexible tube; a holding member that holds the flexible tube; and a check valve provided in the flexible tube.

The coronary artery bypass grafting device according to the present invention is a device for holding the heart in a predetermined position. The coronary artery bypass grafting device according to the present invention includes a plurality of suction cup portions. Thus, the device may adjust the position of the heart from a plurality of directions. The device includes the plurality of suction cup portions to allow the heart to be reliably held in the predetermined position. Further, the device includes the plurality of attachment members having the check valves, and thus even if one suction cup portion is detached from the heart, as for the other suction cup portion attached on the heart, the vacuum breakdown is prevented, allowing the heart to be held by the other suction cup portions. This allows an anastomosis procedure in coronary artery bypass grafting to be performed in a stable manner.

In the present invention, the check valve is a valve adapted to be closed when the backflow of a fluid flowing from a base end side (the side of a suction source) to a tip end side (the side of the suction cup portion) of the check valve without external operation. Providing such a check valve, when a suction cup portion is detached from the subject to be attached, since the pressure inside thereof is relatively positive pressure with respect to the pressure in the suction cup portion attached thereon and the backflow is occurred by the differential pressure therebetween eliminates the need for an operator to open and close the check valve and the check valve provided in the attachment member attached on the subject to be attached is closed state so as to keep the pressure inside the attached suction cup portion, that is, the vacuum breakdown is prevented. This allows an operation during the coronary artery bypass grafting to be performed with greater safety.

For example, in the present invention, the check valve may have a couple of valve bodies which is in contact with each other at tips of the valve bodies and is to be a closed state, and be adapted to be opened when the base end side of the check valve is in a negative pressure with respect to the suction cup portion, and closed when the base end side of the check valve is relatively in a positive pressure with respect to the suction cup portion. In the present invention, the check valve may be a duckbill valve.

In the present invention, the check valve provided in the flexible tube provided with the suction cup portion may be adapted to vibrate and generate a leak sound when the suction cup portion attached to the subject to be attached under a predetermined suction pressure is detached with the suction pressure being applied. This allows occurrence of a detachment of the suction cup portion to be quickly reported to the operator, thereby allowing the procedure by the coronary artery bypass grafting to be performed with greater safety. Also, in the present invention, the check valves for the prevention of the vacuum breakdown and for the generation of the leak sound may be provided separately. Thus, for example, the check valve for the prevention of the vacuum breakdown can be formed by the material with low hardness to improve the deforming ability thereof, the adhesiveness between the couple of valve bodies, and the ability for preventing the vacuum breakdown, while the check valve for the generation of the leak sound can be formed by the material with high hardness to make easier to vibrate and thus to generate the leak sound with higher frequency.

In the coronary artery bypass grafting device according to the present invention, at least one of the attachment members may further include an auxiliary member used for placing the suction cup portion in the predetermined position on the subject to be attached. This allows the suction cup portion to be more reliably placed in the predetermined position using the auxiliary member.

In the coronary artery bypass grafting device according to the present invention, the device may include at least three attachment members. This allows the suction cup portions to be placed in three or more positions on a heart wall surface. This restrains torsion of the heart as compared with the suction cup portions being placed in two positions only. This allows the heart to be more reliably held in the predetermined position. This allows the anastomosis in the coronary artery bypass grafting to be performed with greater safety.

In the coronary artery bypass grafting device according to the present invention, the device may include a connecting member that connects the suction cup portion and the flexible tube between the suction cup portion and the flexible tube, and the connecting member is adapted to allow one of the suction cup portion and the flexible tube to move relative to the other. In the coronary artery bypass grafting device, the connecting member may communicate with the suction cup portion and the flexible tube, and be adapted so that the orientation of one of the suction cup portion and the flexible tube is variable relative to the other. This allows the attitude of the one of the suction cup portion and the flexible tube to with respect to the other to be freely varied. This increases the degree of freedom of movement of the attachment member when the position is adjusted. This allows the position of the heart to be more reliably adjusted.

In the coronary artery bypass grafting device according to the present invention, the connecting member may include a bellows tube that communicates with the suction cup portion and the flexible tube. This allows one of the suction cup portion and the flexible tube to reliably move relative to the other to increase the degree of freedom of relative orientation.

In the coronary artery bypass grafting device according to the present invention, an angular movable range of the flexible tube relative to the suction cup portion may be not less than 30 degrees and not more than 180 degrees in a horizontal plane parallel to an attachment surface of the suction cup portion. In the coronary artery bypass grafting device according to the present invention, an angular movable range of the flexible tube relative to the suction cup portion may be not less than 30 degrees and not more than 180 degrees in a vertical plane perpendicular to the attachment surface of the suction cup portion. This allows the heart to be reliably held in the predetermined position while allowing the position of the heart to be adjusted. In the specification, the angular movable range refers to a range of angles in which the flexible tube can move relative to the suction cup portion.

In the coronary artery bypass grafting device according to the present invention, the suction cup portion may further include: a communication opening that communicates with the flexible tube; and a plurality of slit-like concaves extending from an end of the suction cup portion toward the communication opening. This provides a device with a lower risk of displacement or fall of the heart. In the present invention, the plurality of concaves may extend substantially perpendicularly (in a suction direction) to the attachment surface of the suction cup portion and be provided in parallel with each other.

In the coronary artery bypass grafting device according to the present invention, the end of the suction cup portion may be softer than the inside of the suction cup portion. In the coronary artery bypass grafting device according to the present invention, the end of the suction cup portion may be formed of a member softer than the inside of the suction cup portion. This allows the suction cup portion to be reliably attached to the heart.

In the coronary artery bypass grafting device according to the present invention, the flexible tube may include a main tube, a branch portion that communicates with the main tube, and a plurality of auxiliary tubes that communicate with the branch portion, and a plurality of suction cup portions may be provided in different auxiliary tubes. This allows a reduction in size of the whole device and also increases controllability of the attachment member.

In the coronary artery bypass grafting device according to the present invention, the device may include three or more auxiliary tubes.

In the coronary artery bypass grafting device according to the present invention, the plurality of suction cup portions may communicate with one suction unit via the flexible tube. This ensures the reduction in size of the whole device. The plurality of attachment members may be adjusted using one suction unit, thereby increasing workability in the procedure. Further, the check valve is provided in the flexible tube, and even if one attachment member is detached from the heart, as for the other attachment members attached to the heart vacuum is not broken, and thus the heart may be held by the other attachment members, thereby increasing safety.

In the coronary artery bypass grafting device according to the present invention, the three or more suction cup portions may communicate with one suction unit via the flexible tube.

In the coronary artery bypass grafting device according to the present invention, the switching member and the check valve may be provided in the flexible tube in this order from the suction cup portion provided in the tip end side of the flexible tube to the base end side, in at least one of the attachment members. Such an arrangement ensures the effects of the check valve, and allows a predetermined suction cup portion to be reliably attached to and detached from the subject to be attached.

In the coronary artery bypass grafting device according to the present invention, the suction cup portion may include a plurality of suction cups in at least one of the attachment members.

According to the present invention, there is also provided a coronary artery bypass grafting device including a suction cup portion in a tip end side of a flexible tube, the suction cup portion including a plurality of suction cups.

The coronary artery bypass grafting device according to the present invention includes the plurality of suction cups in the tip end side of one flexible tube, and thus has good followability in attachment to a curved portion besides to a substantially planar portion on the heart wall surface, thereby allowing the heart to be more reliably held in the predetermined position. This allows the anastomosis in the coronary artery bypass grafting to be performed with greater safety.

In the coronary artery bypass grafting device according to the present invention, the shape of the suction cup may be substantially circular.

According to the present invention, there is provided a method for surgically treating the heart using the above described coronary artery bypass grafting device.

According to the method of the present invention, a plurality of suction cup portions can be attached to the heart, and thus the suction cup portions can be attached to a plurality of positions on the heart to hold the heart in a stable manner. when a suction cup portion is detached from the subject to be attached, since the pressure inside thereof is relatively positive pressure with respect to the pressure in the suction cup portion attached thereon and the backflow is occurred by the differential pressure therebetween, the check valve provided in the attachment member attached on the subject to be attached is closed state so as to keep the pressure inside the attached suction cup portion, that is, the vacuum breakdown is prevented. This allows a procedure on the heart to be performed with safety.

Specifically, the method of the present invention may include: placing one suction cup portion in a predetermined position on a heart wall surface when the heart is in a first position; applying a suction pressure to the one suction cup portion and attaching the one suction cup portion to the predetermined position; placing the other suction cup portion in the other position on the heart wall surface; applying a suction pressure to the other suction cup portion by a suction source that applies the suction pressure to the one suction cup portion and attaching the other suction cup portion to the other position; pulling and holding one holding member that holds a flexible tube provided with the one suction cup portion and the other holding member that holds a flexible tube provided with the other suction cup portion to hold the heart in a second position; and surgically treating the heart in the second position.

The method of the present invention may also include: placing one suction cup portion in a predetermined position on a heart wall surface when the heart is in a first position; applying a suction pressure to the one suction cup portion and attaching the one suction cup portion to the predetermined position; placing another suction cup portion in another position on the heart wall surface; applying a suction pressure to another suction cup portion by a suction source that applies the suction pressure to the one suction cup portion and attaching another suction cup portion to another position; placing a further suction cup portion in a further position on the heart wall surface; applying a suction pressure to the further suction cup portion by a suction source that applies the suction pressure to the one suction cup portion and attaching the further suction cup portion to the further position; pulling and holding one holding member that holds a flexible tube provided with the one suction cup portion, another holding member that holds a flexible tube provided with another suction cup portion, and a further holding member that holds a flexible tube provided with the further suction cup portion to hold the heart in a second position; and surgically treating the heart in the second position.

In the method of the present invention, at least one of the attachment members may further include an auxiliary member used for placing the suction cup portion in a predetermined position on a subject to be attached, and the above described placing one suction cup portion in the predetermined position on the heart wall surface may include placing the one suction cup portion in the predetermined position with the auxiliary member.

According to the present invention, there is provided a coronary artery bypass grafting device that can adjust the position of the heart with little displacement or fall of the heart in an affected area that is difficult to anastomose, and perform an anastomosis with safety.

BRIEF DESCRIPTION OF THE DRAWINGS

The above and other objects, advantages and features of the present invention will be more apparent from the following description taken in conjunction with the accompanying drawings, in which.

BEST MODE FOR CARRYING OUT THE INVENTION

Figure 1:
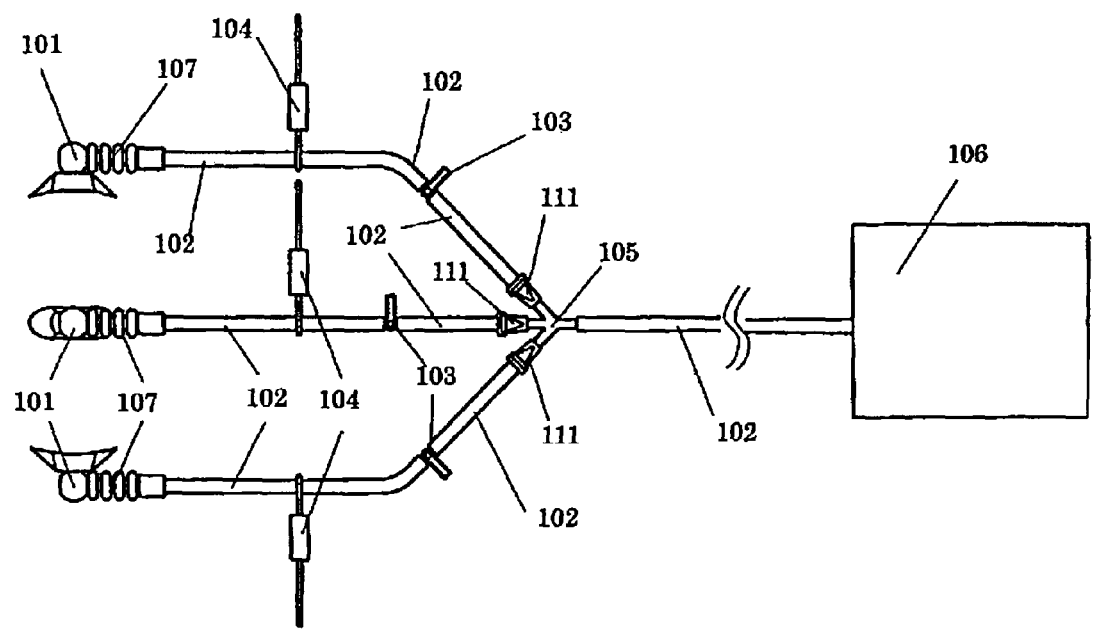
FIG. 1 is a drawing schematically showing a configuration of a coronary artery bypass grafting device related to an embodiment.

Embodiments of the present invention will be described with reference to drawings as follows. Here, like reference numerals or characters will be given to designate the common components throughout the figures thereof, and detailed descriptions thereon will not be appropriately represented in the following descriptions.

A coronary artery bypass grafting device described below is an instrument of fixing a heart at a predetermined position. This device is preferably used when a heart undergoes a predetermined treatment, for example, coronary artery bypass grafting and the like.

First Embodiment

FIG. 1 is a drawing showing an example of a coronary artery bypass grafting device of the present invention. The coronary artery bypass grafting device shown in FIG. 1 has a plurality of, preferably more than or equal to three, attachment members. FIG. 1 exemplifies a configuration provided with three attachment members.

An attachment member includes a flexible tube 102, a suction cup portion 101 provided at a side of a tip of the flexible tube 102, a three-way cock 103 being an opening and closing member provided to the flexible tube 102, a holding member 104 of holding the flexible tube 102 and a duckbill valve 111 being a check valve provided to the flexible tube 102. Here, FIG. 1 exemplifies a configuration for all three attachment members to include respective duckbill valves 111, but at least one of a plurality of attachment members may include a duckbill valve 111.

In the coronary artery bypass grafting device shown in FIG. 1, the flexible tube 102 includes a main tube, a triple joint 105 being a branching part in communication to the main tube and three auxiliary tubes in communication to the triple joint 105, that is, each of the three attachment members has a mutually different auxiliary tube. Here, the triple joint 105 is configured to bring four pipes, one pipe for the main tube side and three pipes for the auxiliary tube sides, into mutual communication in the branching part. Therefore, auxiliary tubes configuring the attachment members are configured to be interconnected each other with a triple joint 105 and the like. In addition, the other end of the flexible tube 102, that is, an end portion of the main tube is connected to a suction source 106. And, the three suction cup portions 101 are connected to a single suction source 106 through a flexible tube 102. The suction source 106 can be, for example, a vacuum pump and the like.

Materials for the flexible tube 102 can be materials such as, for example, polyurethane resin, flexible vinyl chloride resin and silicone resin and the like. In addition, the flexible tube 102 is formed by, for example, extrusion molding. Sizes of the flexible tube 102 can be configured by the entire length of, for example, more than or equal to 50 mm, preferably more than or equal to 100 mm, and the inner diameter of, for example, more than or equal to 2 mm, preferably more than or equal to 4 mm. In addition, a reinforcing member such as a metal coil, film or fabric and the like may be employed to reinforce the flexible tube 102. Thus, interruption of suction due to a kink can be prevented. Therefore, the kink resistant nature of the flexible tube 102 can be improved.

In the coronary artery bypass grafting device shown in FIG. 1, the suction cup portion 101 is provided at the tip end side of the flexible tube 102. In particular, as aforementioned, the three suction cup portions 101 are respectively connected to the end portions of the three auxiliary tubes branching from a single main tube. The suction cup portions 101 suctions with the suction source 106 through the flexible tubes 102. Suction causes attachment onto a surface of a subject to be attached and sucked.

Here, the subject to be attached is a heart. This can make the suction cup portion 101 become a material excellent in the tight contact nature to a heart wall surface. The material of the suction cup portion 101 can be, for example, an elastomeric substance. This arrangement will give rise to sufficient fitting onto heart wall surfaces so that the tight contact nature can be ensured. In particular, the material of the suction cup portion 101 is preferably silicone resin, stylene-ethylene-butadiene-stylene resin and elastomer such as urethane elastomer and the like.

In addition, the suction cup portion 101 can be shaped into a pad. The shape of the suction cup portion 101 in a plan view can be, for example, circular. In addition, not only circular shape but also approximately oval shape as shown in the drawings can be employed. Being shaped oval instead of shaped plane, the suction cup portion 101 can be brought into attachment onto a heart wall surface at the largest contact area without suctioning blood vessels on the hear wall surface.

In addition, sizes of the suction cup portion 101 can be in terms of diameter, for example, more than or equal to 5 mm, preferably more than or equal to 10 mm in case of the plane shape being circular. Thus, the suction cup portion 101 can be brought into attachment onto a heart wall surface more stably. In addition, the diameter of the suction cup portion 101 can be made to be, for example, less than or equal to 60 mm, preferably less than or equal to 50 mm. Thus, the suction cup portion 101 can be made compact and therefore workability can be improved further also in the case where a plurality of suction cup portions 101 are arranged on a heart wall surface.

In addition, in case of the plane shape of the suction cup portion 101 being approximately an oval shape, the length thereof in the longitudinal direction can be made, for example, more than or equal to 20 mm, preferably more than or equal to 30 mm, from the point of view for causing the suction cup portion 101 to be brought into attachment onto the heart wall surface more stably. In addition, from the point of view of further improving workability, the length in the longitudinal direction can be made, for example, less than or equal to 60 mm, preferably less than or equal to 50 mm. Moreover, the length of the suction cup portion 101 in the short side direction can be made, for example, more than or equal to 5 mm, preferably more than or equal to 10 mm, from the point of view for causing the suction cup portion 101 to be brought into attachment onto the heart wall surface more stably. In addition, from the point of view of further improving workability, the length in the short side direction can be made, for example, less than or equal to 30 mm, preferably less than or equal to 20 mm. In addition, the height of the suction cup portion 101 can be made, for example, not less than 5 mm and not more than 30 mm.

Configurations of the length of the suction cup portion 101 as described above can ensure to bring the suction cup portion 101 into attachment onto a heart surface so that the heart is fixed. In addition, as the suction cup portion 101 is being stably fixed onto the heart surface, treatment workability can be secured.

The shape of the suction cup portion 101 of the coronary artery bypass grafting device shown in FIG. 1 is preferably made to be in a tapered shape with the diameter getting larger toward the end portion of the suction cup portion 101. This can restrain the suction cup portion 101 from being deformed inward due to suction pressure at the time of suction contact with the heart wall. In addition, the sizes or the shapes of a plurality of suction cup portions 101 are not necessarily uniform respectively, but, for example, the suction cup portion 101 that is caused to fit into the cardiac apex of a heart may be made the largest. This arrangement can ensure a heart to be held at a predetermined position.

In addition, the suction cup portion 101 may be provided with an opening on the attachment surface. The opening can be configured to be in communication with the flexible tube 102. In addition, a mesh and the like with a plurality of small holes which covers the opening of the suction cup portion 101 may be disposed. At this time, the heart wall surface will be configured to contact the suction cup portion 101 through the mesh.

In addition, a convex part may be provided around the suction opening so that space is provided between there and the suction opening. This can prevent decrease in the suction area. Consequently, the suction power in the suction cup portion 101 can be caused to improve. Material of the mesh and the like can be polyester fabric such as polyethylene terephthalate and the like, polyamide fabric such as nylon and the like or water-absorbing unwoven fabric or cotton.

Figure 4:
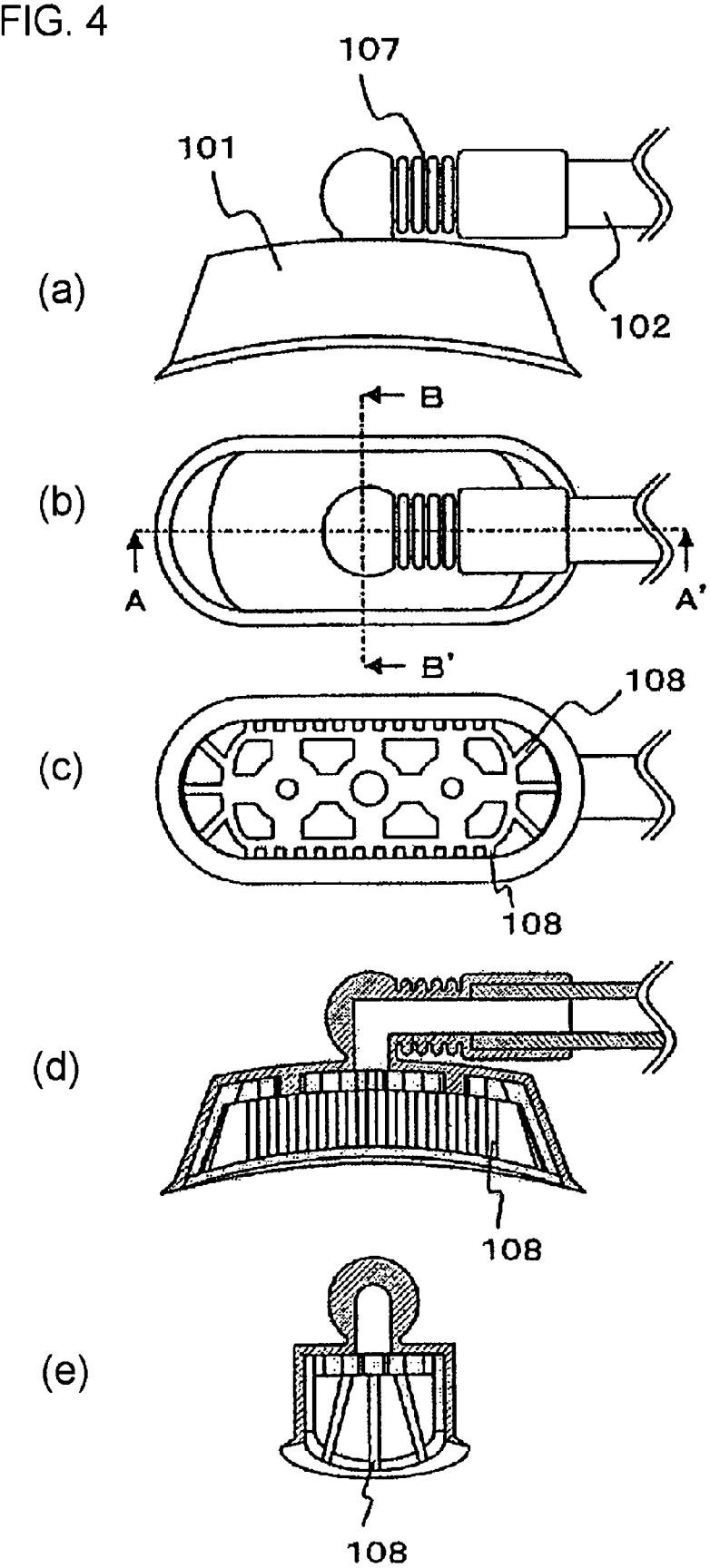
FIG. 4 is a drawing schematically showing a configuration of a suction cup portion of a coronary artery bypass grafting device related to an embodiment.

In addition, a plurality of concave slits (slits 108) are preferably formed in the inner surface of the opening provided in the suction cup portion 101. FIG. 4(a) to FIG. 4(e) are drawings to describe a configuration of a suction cup portion 101 having slits. FIG. 4(a) is a front view of the suction cup portion 101. FIG. 4(b) is a top view of the suction cup portion 101. FIG. 4(c) is a bottom view of the suction cup portion 101. FIG. 4(d) is a sectional view along the line A to A' in FIG. 4(b). In addition, FIG. 4(e) is a sectional view along the line B to B' in FIG. 4(b).

FIGS. 4A to 4E exemplify a case of a suction cup portion 101 being a rectangle provided with R in corners. In this configuration, the suction cup portion 101 is further provided with a communication opening (not shown in the drawings) in communication to the flexible tube 102 and a plurality of slit-shaped concave portions (slits 108) extending toward the communication opening from the end portion of the suction cup portion 101. The slits 108 are grooves formed in the inner surface of the suction cup portion 101. Providing the slits 108, liquid inside the suction cup portion 101 can be discharged efficiently to the flexible tube 102 from the slits 108 via the communication opening. Consequently, the discharge route can be made never to be blocked by liquid that might collect inside the suction cup portion 101 and the draining effects of draining body fluid and the like on tissue surfaces can be derived, which can prevent the suction cup portion 101 from lateral sliding against tissues. In addition, as shown in FIG. 4(c) to FIG. 4(e), a plurality of concave slits (slits 108) can be configured to extend in a direction (suction direction) substantially perpendicular to the attachment surface and to be provided in substantially parallel each other.

In addition, a plurality of slits 108 extend from the center of the suction cup portion 101 to its circumference and are formed radially. This allows efficient discharge of liquid in the suction cup portion 101 from the interior to the exterior of the opening. In addition, a plurality of slits 108 may be provided in the circumferential direction of the inner surface of the suction cup portion 101. Moreover, the slits 108 are preferably formed to reach in the vicinity of the end portion of the suction cup portion 101. This will give rise to an effect that suction pressure can be applied to reach the end portion of the suction cup portion 101 in an ensured fashion in addition to the above described draining effect. Therefore, the suction power can be caused to improve.

The width of the slits 108 is preferably, for example, not less than 0.2 mm and not more than 1 mm and the depth thereof is preferably not less than 0.5 mm and not more than 5 mm. This can restrain tissues from completely infiltrating into the slits 108 to deteriorate the draining effects of the slits. This can improve the draining effects of the suction cup portion 101.

Figure 5:
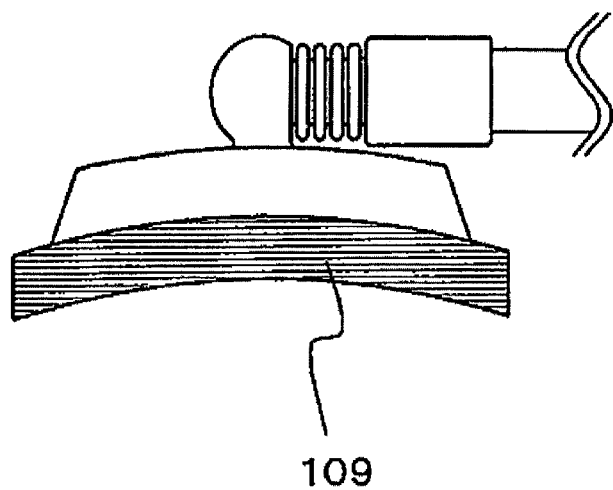
FIG. 5 is a drawing schematically showing a configuration of a suction cup portion of a coronary artery bypass grafting device related to an embodiment.

In addition, in the coronary artery bypass grafting device shown in FIG. 1, the end portion of the suction cup portion 101 is preferably a soft or pliable site. FIG. 5 is a sectional view schematically showing a configuration of thus configured suction cup portion 101. In FIG. 5, the end portion of the suction cup portion 101 is provided with a pliable member 109 and therefore the end portion of the suction cup portion 101 configures a pliable portion. As shown in FIG. 5, the tip end portion, in particular the outer periphery of the opening, of the suction cup portion 101 is provided with a pliable member 109 and thereby the end portion of the suction cup portion 101 can be configured by a member softer than the interior of the suction cup portion 101. In addition, the end portion of the suction cup portion 101 is made softer than the interior of the suction cup portion 101. Thus, the nature of the suction cup portion 101 to follow pliable tissues is improved so that the suction power can be caused to improve.

As a method of making the end portion of the suction cup portion 101 pliable, provision of the end portion of the suction cup portion 101 that is made thinner than the portions other than the end portion and disposition of another pliable member can be employed. As another method of deriving pliability, a method of making hardness of the end portion lower by, for example, more than or equal to 20% than hardness of the suction cup portion 101 can be employed. As a material like this, the one having the same hardness as the above described suction cup portion 101 with only material having been made low and a closed-cell sponge or a gel material and the like can be employed.

Now back to FIG. 1, the coronary artery bypass grafting device is provided with a holding member 104 of holding the flexible tube. The holding member 104 adjusts the position of the suction cup portion 101 to hold it at a predetermined position. The holding member 104 is formed by, for example, extrusion molding.

The holding member 104 should be, for example, a stick or tube member. Thus, the end portion of the holding member 104 being grasped to implement remote operation ensures disposition of the suction cup portion 101 to a predetermined location. In addition, at this time, the sizes of the holding member 104 can be configured by the entire length of, for example, more than or equal to 200 mm, preferably more than or equal to 300 mm. Thus the suction cup portion 101 can be held more stably. In addition, there is no particular limits to the upper limit for the entire length of the holding member 104, but from the point of view of ensuring a field of view more sufficiently at the time of treatment, for example, less than or equal to 1000 mm, preferably less than or equal to 800 mm, can be taken. In addition, the outer diameter of the holding member 104 can be made, for example, more than or equal to 2 mm, preferably more than or equal to 3 mm. This enables hardness of the holding member 104 to be improved further. In addition, there is no particular limits to the upper limit for the outer diameter of the holding member 104, but from the point of view of making the grafting device compact, for example, less than or equal to 10 mm, preferably less than or equal to 8 mm, can be taken.

As the material of the holding member 104, a material is preferably unbreakable. This can ensure adjustment of the position of the suction cup portion 101 to hold the suction cup portion 101 at a desired position. The material of the holding member 104 can be metal, for example, stainless steel and the like. In addition, resin materials such as polyamide resin, polycarbonate resin, rigid vinyl chloride resin, silicone resin and the like can be employed. In case of employing an elastomer such as silicone resin and the like, appropriate expansion of the holding member enables absorption of heart beats so that the heart can be held more stably.

In addition, in the coronary artery bypass grafting device shown in FIG. 1, the flexible tubes 102 in communication to a plurality of the suction cup portions 101 brought into attachment onto a heart wall surface and respective holding members 104 may be fixed to a rib retractor and the like with traction forceps and the like. By fixing the flexible tubes 102 and the holding members 104 to a rib retractor and the like with traction forceps and the like to adjust the position of a heart, the position of the heart can be adjusted from not only one direction but also from a plurality of directions. Therefore, displacement of a heart during anastomosis, or risks of fall of a heart can be caused to decrease. In addition, the holding member 104 may be, for example, configured to be able to slide at any site on a flexible tube 102, and may be configured to be able to be fixed to the flexible tube 102 at the time of pulling the holding member 104. This can improve pulling operability.

In addition, in the coronary artery bypass grafting device shown in FIG. 1, by adjusting the three-way cock 103 provided in the main tube to leave it in an interrupted state so as not to bring the suction source 106 into communication to the auxiliary tubes, and adjusting the three-way cock 103 after bringing the suction cup portion 101 into fitting onto the heart wall surface to bring the suction cup portion 101 into communication to the flexible tube 102, the heart wall can be sucked with the suction cup portion 101. In addition, removal of the suction cup portion 101 from the heart wall can be implemented by adjusting the three-way cock 103, interrupting communication to the suction source 106 and being released with the atmosphere.

Next, in the coronary artery bypass grafting device shown in FIG. 1, the connecting member 107 is a member that is provided between the suction cup portion 101 and the flexible tube 102, is in communication to the suction cup portion 101 and the flexible tube 102 and brings the both into connection. In addition, the connecting member 107 makes one of the suction cup portion 101 and the flexible tube 102 movable against the other. For example, the both may be brought into connection with the connecting member 107 so that the flexible tube 102 can move arbitrarily against the suction cup portion 101.

In FIG. 1, the posture of one of the suction cup portion 101 and the flexible tube 102 is configured to made variable against the other. In particular, the direction of one of the suction cup portion 101 and the flexible tube 102 is made variable against the other. Thus, the flexible tube 102 is movable against the suction cup portion 101, therefore can absorb torsion stress at the time of pulling the flexible tube 102 in the direction different from the original connecting direction as well as stress applied to the suction cup portion 101 by heart beats, prevent release of the suction cup portion 101 from the heart wall surface and improve safety. As the connecting member 107 for the flexible tube 102 to derive arbitrary movability against the suction cup portion 101, a bellows tube in communication to the suction cup portion 101 as well as the flexible tube 102, for example, can be employed.

In addition, the connecting member 107 may be configured to make an angular movable range of the above described flexible tube being not less than 30 degrees and not more than 180 degrees against the above described suction cup portion, in the horizontal plane in parallel to the attachment surface of the suction cup portion 101. In addition, it may be configured to make an angular movable range of the above described flexible tube being not less than 30 degrees and not more than 180 degrees against the above described suction cup portion, in the perpendicular plane perpendicular to the attachment surface of the suction cup portion 101. By making the angular movable range to be more than or equal to 30 degrees, movement freedom of the flexible tube 102 against the suction cup portion 101 can be ensured sufficiently. In addition, by making the angular movable range to be less than or equal to 180 degrees, an occurrence of torsion on the heart wall surface attached to the suction cup portion 101 can be restrained so that holding is ensured.

In addition, the connecting member 107 is preferably connected in the vicinity of the center of the suction cup portion 101 in a plan view. This can give rise to a configuration that applies uniform stress to the suction cup portion 101 when the flexible tube 102 is pulled. Consequently, damages to a heart at the time of suction can be prevented. In addition, the connecting member 107 preferably brings the both of the suction cup portion 101 and the flexible tube 102 into connection so that the attachment surface of the suction cup portion 101 will be horizontal in the extending direction of the flexible tube 102. Thereby, bulkiness of the suction cup portion 101 can be restrained. Therefore, a heart can become fixable in an ensured fashion in a limited space.

Next, in the coronary artery bypass grafting device shown in FIG. 1, the flexible tube 102 is provided with an opening and closing member. The opening and closing member can be configured by a three-way cock 103 as shown in FIG. 1. More than or equal to one three-way cock 103 can be provided to each auxiliary tube. This enables adjustment of the respective three-way cocks 103 individually to adjust the suction state of each suction cup portion 101.

In addition, in case of adopting the three-way cock 103 as the opening and closing member, a stopper may be provided to prevent rotation to one direction so as to enable limitation of adjustment only in the two directions. This will enable rotation adjustment of the cock to perform:

i) an ensured suction operation when a heart wall undergoes suction with the suction cup portion 101, and ii) an operation of interrupting and releasing the suction cup portion 101 from the suction source 106 with the atmosphere when to remove the suction cup portion 101 from the heart wall.

In addition, as a configuration of enabling the opening and closing member to be adjustable only in the two directions, besides the configuration of rotating a cock such as a three-way cock 103, for example, a member corresponding to the cock may be configured to be slidable in the direction perpendicular to the flexible tube so that the above described operations i) and ii) can be performed.

The coronary artery bypass grafting device shown in FIG. 1 has at least more than or equal to three attachment members. In case of employing one attachment member, since a heart is held at only one site, the movable range of the attached heart is large. In addition, since the heart is held only from one direction, the heart has a strong force to return to the original position against the attachment member, displacement or fall of the heart is apt to occur. By providing a plurality of attachment members, the heart can be held from a plurality of directions. Therefore, the force of the heart that intends to return to the original position is dispersed so that the heart can be held stably in a predetermined position.

In addition, in the coronary artery bypass grafting device shown in FIG. 1, more than or equal to three attachment members are employed. In case of employing two attachment members, there remains freedom of the movable range of the attached heart. By employing more than or equal to three attachment members, a heart can be clip and held from more than or equal to three directions. In addition, employment of more than or equal to three attachment members ensures a sufficient area of contacting the heart wall surface and can attach and hold the heart sufficiently. Therefore, the heart can be held more stably at a predetermined position.

Next, in the coronary artery bypass grafting device shown in FIG. 1, the flexible tube 102 is provided with a check valve with the direction from the suction cup portion 101 to the suction source side being set as the forward direction.

The check valve is configured to be able to restrain a back-flow via the check valve without undergoing operations from outside. That is, the check valve has a function of circulating fluid in only one direction. In particular, when the base end side of the check valve (the side of the suction source 106) has negative pressure to the side of the suction cup portion 101, an open state occurs so that the suction cup portion 101 is attached to the heart wall surface with suction pressure. On the other hand, when the base end side of the check valve (the side of the suction source 106) has relatively positive pressure to the side of the suction cup portion 101, a closed state is configured to occur.

Such a check valve has, for example, a couple of valves so as to be brought into contact each other at the tip end side of the suction cup portion 101 and a closed state is configured to occur. Under a closed state, since the valves are continuously inclined inward from the wall surface side of the flexible tube and are brought into contact each other at the base side, that is the end portion of the side of the suction source 106, to give rise to tight contact, the flow route of fluid is interrupted. In addition, under an open state, since the tip of the valves is made separate, a path for fluid is formed between the valves.

The check valve can be a duckbill valve 111 as shown in FIG. 1. One duckbill valve 111 can be provided to each auxiliary tube. The duckbill 111 can be provided in its outside with a housing that encloses the duckbill valve 111 so as to be connectable to the auxiliary tube or the branching part (triple joint 105). Thereby, even if one suction cup portion 101 is released by chance from a heart, suction pressure applied to the interior of the flexible tube 102 at the side of the suction source 106 by the duckbill valve 111 disposed in the flexible tube 102 in communication to another suction cup portion 101 will get higher than, that is, will be relatively in positive pressure with respect to the suction pressure from the duckbill valve 111 to inside the suction cup portion 101. The difference pressure generates a back-flow of the air, and by the back-flow, the check valve is closed so as to retain suction pressure inside the suction cup portion 101, the heart can be held. In addition, at the time when the suction cup portion 101 is released, a person in charge of operations and the like is not required to do any operation in particular to the duckbill valve 111, but the back-flow can be interrupted automatically. Consequently, safety of anastomosis operation can be improved.

Materials for the check valve may be, for example, silicone resin, acrylonitrile rubber, isoprene rubber and elastomers such as urethan elastomer and the like. In addition, the check valve is not limited to the duckbill valve, but may be another check valve in such as umbrella form and the like. These check valves can be molded by compression molding and the like. In addition, materials for the housing to enclose the check valves may be, for example, rigid vinyl chloride resin and polycarbonate resin. These housings can be molded by injection molding and the like. A housing can be configured by two components so as to be able to enclose the check valve, and the housing having two components can be assembled by, for example, ultrasonic sealing under a state of enclosing the check valve.

In addition, the check valve may be configured to notify the person in charge of operations as an alert in form of leak sounds generated by vibration of the check valve provided to the same flexible tube 102 (auxiliary tube) as the flexible tube 102 (auxiliary tube) to which the a released suction cup portion 101 is provided when a suction cup portion 101 attached onto a heart wall surface under predetermined suction pressure has been released from the heart in a state where the suction pressure being given. Moreover, the check valve may be configured to generate leak sounds with frequencies from 100 Hz to 10 kHz with vibration of the check valve in order to notify the person in charge of operations as an alert of the incident that a suction cup portion 101 attached onto the heart wall surface under suction pressure of −200 mmHg to −400 mmHg has been released from the heart. Thus, a treatment by coronary artery bypass grafting can be implemented further safely. Also, the check valves for the prevention of the vacuum breakdown and for the generation of the leak sound may be provided separately. For example, the check valve for the prevention of the vacuum breakdown can be formed by the material with low hardness to improve the deforming ability thereof, the adhesiveness between the couple of valve bodies, and the ability for preventing the vacuum breakdown, while the check valve for the generation of the leak sound can be formed by the material with high hardness to make easier to vibrate and thus to generate the leak sound with higher frequency.

In addition, as the coronary artery bypass grafting device shown in FIG. 1, the attachment member can be configured by the opening and closing member (three-way cock 103) and the check valve (duckbill valve 111) being provided to the flexible tube 102 in this order in series at the back side than the suction cup portion 101 (that is, the side of the suction source 106) provided in the tip end side of the flexible tube 102. Thereby, without deteriorating an effect of the check valve that a heart can be held by another suction cup portion 101 in the case where one suction cup portion 101 is released from the heart, operations of the opening and closing member enable implementation of air release inside the suction cup for removing the suction cup portion 101 from the heart wall. Conversely, in case of providing the flexible tube with the opening and closing member in series at the back side than the check valve (the base end side, that is, the side of the suction source 106), implementation of air release inside the suction cup for removing the suction cup portion 101 from the heart wall by operations of the opening and closing member is interrupted by the check valve, which is not preferable.

Accordingly, in the coronary artery bypass grafting device shown in FIG. 1, at least more than or equal to three attachment members are employed so that heart position adjustment with little heart displacement or heart fall is performed so as to enable implementation of anastomosis safely compared with the device to date that only has less than or equal to two attachment members.

In addition, at least one among more than or equal to three attachment members has the duckbill valve 111. Therefore, at the time when the suction cup portion 101 provided in the attachment member having a duckbill valve 111 or the suction cup portion 101 in the other attachment members are released from the heart wall surface, the duckbill valve 111 can prevent a back-flow from going through this.

Moreover, in FIG. 1, since all the three attachment members are provided with duckbill valves 111, back-flows via the duckbill valves can be restrained effectively as to all the flexible tubes.

In addition, the suction cup portion 101 is provided with a plurality of concave slits 108 (FIG. 4) so that lateral sliding of the suction cup portion 101 against tissues can be prevented and, moreover, suction pressure can be applied to reach the end portion of the suction cup portion 101 in an ensured fashion and, therefore, the suction power can be improved. In addition, by providing the end portion of the suction cup portion 101 with a pliable member 109 to make the portion pliable, the nature of following the pliable tissues can be improved and the suction power can be improved.

Figure 2:
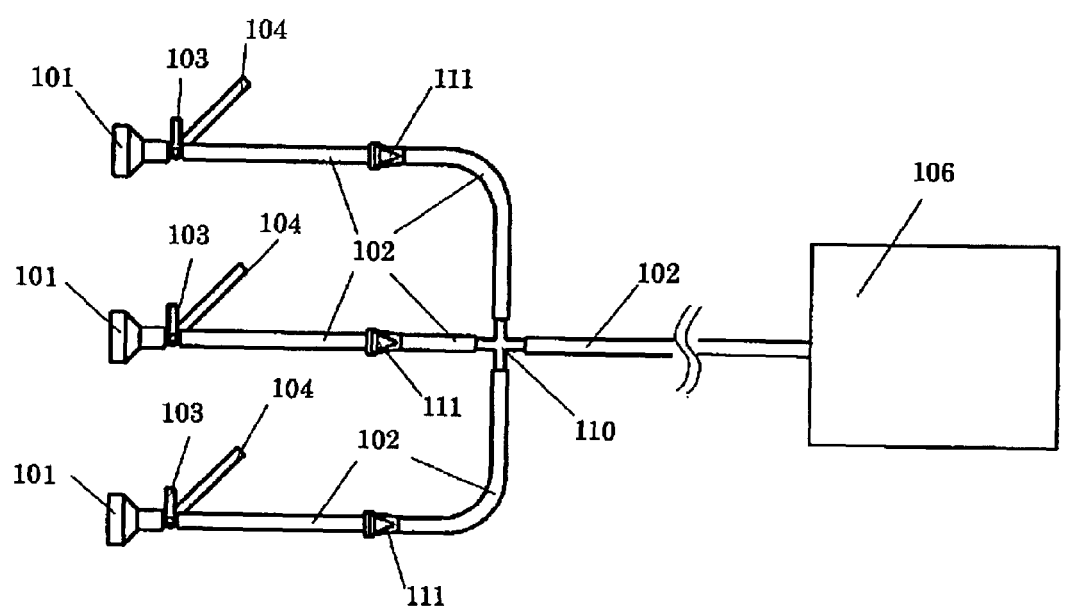
FIG. 2 is a drawing schematically showing a configuration of a coronary artery bypass grafting device related to an embodiment.
Figure 3:
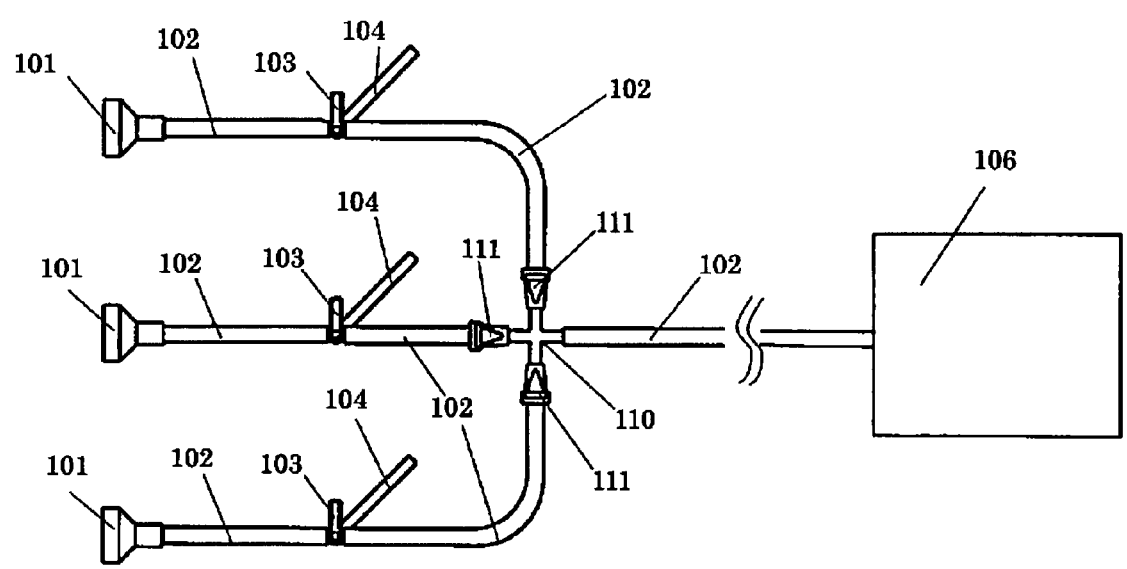
FIG. 3 is a drawing schematically showing a configuration of a coronary artery bypass grafting device related to an embodiment.

FIG. 2 and FIG. 3 are drawings schematically showing other configuration examples of the coronary artery bypass grafting device. The configuration of the coronary artery bypass grafting device shown in FIG. 1 is also applicable to the configuration shown in the following drawings. In addition, the configuration shown in FIG. 2 or FIG. 3 is applicable to the coronary artery bypass grafting device shown in FIG. 1 as well. As shown in FIG. 2 or FIG. 3, an X-type joint 110 may be used in place of the triple joint 105 shown in FIG. 1.

In the coronary artery bypass grafting device shown in FIG. 2, the opening and closing member is disposed in the vicinity of the suction cup portion 101. In addition, the connecting member 107 is not provided between the suction cup portion 101 and the flexible tube 102. In addition, the attachment surface of the suction cup portion 101 is fixed in perpendicular to the extending direction of the flexible tube 102.

As the opening and closing member configured to bring the suction cup portion 101 and the flexible tube 102 into connection so that the suction cup portion 101 is in communication to the flexible tube 102, two-way cock or the three-way cock 103 shown in the drawing can be employed. This can ensure the ease and convenience of operations of the coronary artery bypass grafting device.

At the time of use of the coronary artery bypass grafting device shown in FIG. 2, at first, the two-way cock or the three-way cock 103 is adjusted so that communication between the suction cup portion 101 and the flexible tube 102 from the suction source 106 is interrupted to cause the suction cup portion 101 to fit into the heart wall surface. Thereafter, by adjusting the two-way cock or the three-way cock 103, the suction cup portion 101 is brought into the state of being in communication to the flexible tube 102. This enables the suction cup portion 101 to suction the heart wall. In addition, removal of the suction cup portion 101 from the heart wall can be implemented by adjusting the three-way cock 103, interrupting to derive a state of the suction cup portion 101 being not in communication to the suction source 106 and being released with the atmosphere.

In addition, the holding member 104 is connected to in the vicinity of the suction cup portion 101. The holding member 104 adjusts positions of the suction cup portion 101. As the material of the holding member 104, a material is preferably unbreakable material. For example, metal such as stainless steel and the like or resin materials such as polyamide resin, polycarbonate resin, rigid vinyl chloride resin, silicone resin and the like may be the material. The position of a heart attached onto the suction cup portion 101 is adjustable by pulling the flexible tube 102 in communication to the three-way cock 103 disposed in the vicinity of a plurality of the suction cup portion 101 attached onto the heart wall surfaces, or the respective holding members 104 disposed in the flexible tube 102.

In the coronary artery bypass grafting device shown in FIG. 2, by disposing the three-way cock 103 and the holding member 104 in the vicinity of the suction cup portion 101, operability for the person in charge of operations can be improved.

In addition, the coronary artery bypass grafting device shown in FIG. 3 is provided with the three-way cock 103 being the opening and closing member and the holding member 104 in the location apart from the suction cup portion 101 in the coronary artery bypass grafting device in FIG. 2. By disposing the three-way cock 103 and the holding member 104 apart and separately from the suction cup portion 101, peripheral bulkiness of the suction cup portion 101 can be caused to decrease. Therefore, even the case where space between the heart and the pericardium being the periphery of the heart is small, there are effects that the site suctioning the heart will not be limited.

Here, in the coronary artery bypass grafting device shown in FIG. 2 and FIG. 3, flexible tubes 102 in communication to a plurality of suction cup portions 101 brought into attachment onto a heart wall surface and respective holding members 104 that are disposed at the three-way cocks 103 being opening and closing members may be pulled and fixed to a rib retractor and the like with forcepts and the like.

Second Embodiment

In the coronary artery bypass grafting device according to the first embodiment, the suction cup portion 101 may be configured by at least two or more subround suction cups. Since the suction cup portion 101 has at least two or more subround suction cups, the device excels in trackability during attachment to a curved surface as well as the substantially flat portion of the heart wall surface, thereby successfully hold the heart at a predetermined position with high accuracy. Furthermore, the attachment to the heart wall surface can be realized on the largest possible contact area without suctioning blood vessels. The differences of the present embodiment from the first embodiment are mainly explained below more concretely by referring to FIG. 6, FIG. 7(a) to FIG. 7(e), and FIG. 8.

Figure 6:
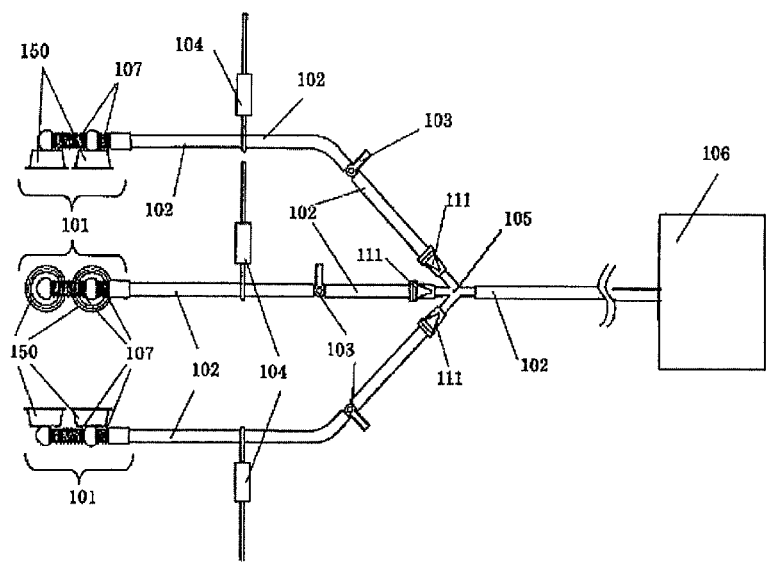
FIG. 6 is a drawing schematically showing a configuration of a coronary artery bypass grafting device related to an embodiment.

FIG. 6 shows an example of a coronary artery bypass grafting device according to the present invention. The coronary artery bypass grafting device shown in FIG. 6 includes plural (three in FIG. 6) attachment members. Each attachment member includes: a flexible tube 102; a suction cup portion 101 having two suction cups 150 attached at the tip end side of the flexible tube 102; a three-way cock 103 as an opening and closing member provided for the flexible tube 102; the holding member 104 for holding the flexible tube 102; and the duckbill valve 111 as a check valve provided for the flexible tube 102.

The suction cup 150 is contained in the suction cup portion 101 and has a subround (subround-shaped) flat portion in FIG. 6. In FIG. 6, the suction cup 150 is contained in one of the suction cup portions 101.

In the coronary artery bypass grafting device shown in FIG. 6, the suction cup portion 101 having two suction cups 150 is provided on the tip end side of the flexible tube 102. Specifically, as described above, the three suction cup portions 101 are connected to the end portion of each of the three auxiliary tubes branched from one main tube. The suction cup portions 101 are suctioned by the suction source 106 through the flexible tube 102. By the suction, the suction cup portions 101 attach to the surface of an object to be attached.

The object to be attached is a heart. Therefore, the suction cup portions 101 having two suction cups 150 can be materials excellent in adhesion to the heart. The material of the suction cup portion 101 can be, for example, an elastic substance. Thus, the suction cup portion 101 can be sufficiently fitted to the heart wall surface, thereby ensuring the adhesion. Specifically, the material of the suction cup portion 101 is preferably a silicone resin, a styrene-ethylene-butadiene-styrene resin, elastomer such as urethane elastomer, and the like.

The suction cup portion 101 may have at least two suction cups 150. Since it includes at least two suction cups 150, it is excellent in trackability during attachment not only to the substantially flat portion but also to the curved surface of the heart wall surface, thereby holding the heart at a predetermined position with high accuracy. Furthermore, the attachment to the heart wall surface can be realized on the largest possible contact area without suctioning blood vessels on the heart wall surface.

When the flat shape of the suction cup 150 is substantially circular, the size of the suction cup 150 of the suction cup portion 101 can be 5 mm or more in diameter, and can be preferable 10 mm or more. Thus, the suction cup 150 can furthermore stably attach to the heart wall surface. The diameter of the suction cup 150 of the suction cup portion 101 can also be, for example, 50 mm or less, and can be preferable 40 mm or less. Thus, with plural suction cups 150, the suction cup portion 101 can be smaller, thereby surely suppressing the obstruction of the suction cup 150 to an operation. Additionally, the height of the suction cup portion 101 can be, for example, 5 mm or more from the view of more stable attachment to the heart wall surface. In downsizing the suction cup portion 101, the height of the suction cup portion 101 can be, for example, 30 mm or less.

With the above-mentioned configuration for the size of the suction cup portion 101, the suction cup portion 101 can surely attach to the surface of the heart, thereby fixing the position of the heart. Furthermore, the effect of an operation can be ensured with the suction cup portion 101 stably fixing on the surface of the heart.

It is preferable that the shape of the suction cup portion 101 of the coronary artery bypass grafting device shown in FIG. 6 is tapered, that is, the diameter of the suction cup portion 101 is to increase toward the end portion of the suction cup 150. Thus, when the suction cup portion 101 is suctioned and contacted with the heart wall surface, the suction cup 150 of the suction cup portion 101 can be prevented from being pulled inside by the suction pressure. The sizes or the shapes of the plural suction cup portions 101 are not limited to the same. For example, the suction cup portion 101 to be fitted to the cardiac apex of the heart can be the largest. Thus, the heart can surely be held at a predetermined position.

The suction cup portion 101 having the suction cup 150 can be provided with an opening on the attachment surface. The opening can be configured to communicating to the flexible tube 102. In addition, there may be meshes having a number of small holes covering the opening of the suction cup portion 101. At this time, the wall surface of the heart is configured to contact to the suction cup portion 101 through the meshes.

Figure 7:
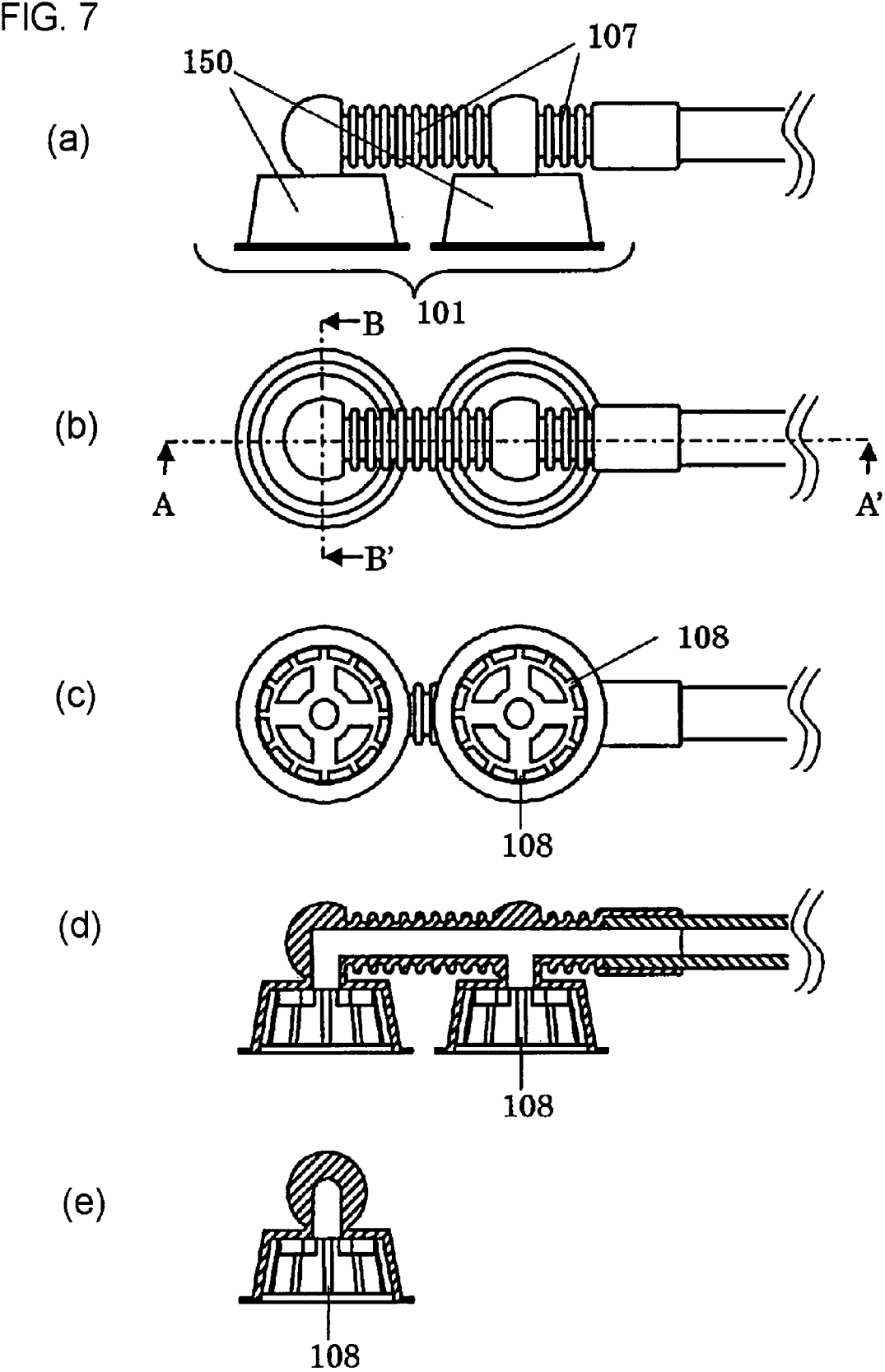
FIG. 7 is a drawing schematically showing a configuration of suction cup portions of a coronary artery bypass grafting device related to an embodiment.

It is preferable that plural concave slits are formed inside the opening of the suction cup portion 101 having the suction cup 150. FIG. 7(A) to FIG. 7(e) are explanatory views of the configuration of the suction cup portion 101 having slits. FIG. 7(a) is a front view of the suction cup portion 101. FIG. 7(b) is a top view of the suction cup portion 101. FIG. 7(c) is a bottom view of the suction cup portion 101. FIG. 7(d) is a sectional view along A to A' shown in FIG. 7(b). FIG. 7(e) is a sectional view along B to B' shown in FIG. 7(b).

FIG. 7(a) to FIG. 7(e) show the cases of the suction cup 150 of the suction cup portion 101. In the configuration, as with the case according to the first embodiment, the suction cup 150 is provided with a communication opening (not shown in the drawings) communicating to the flexible tube 102 and plural concave portions (slits 108) extending from the end portion of the suction cup 150 to the communication opening. The slits 108 are grooves formed inside the suction cup portion 101. By providing the slits 108, from the slits 108 through the communication opening, the liquid in the suction cup portion 101 can be efficiently drained to the flexible tube 102. Therefore, the suction cup portion 101 can be prevented from containing a liquid to be blocked the drain path and the draining effects of draining body fluid and the like on tissue surfaces can be derived, which can prevent the suction cup portion 101 from lateral sliding against tissues. Furthermore, as shown in FIG. 7(c) to FIG. 7(e), the concave portions of the plural slits extend substantially perpendicularly (in the suction direction) to the attachment surface, and are substantially parallel to each other.

Figure 8:
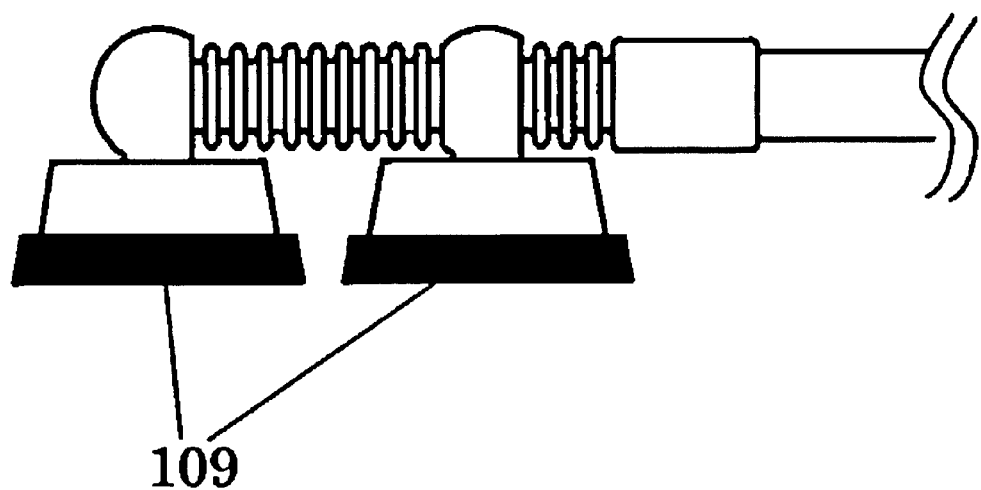
FIG. 8 is a drawing schematically showing a configuration of suction cup portions of a coronary artery bypass grafting device related to an embodiment.

In the coronary artery bypass grafting device shown in FIG. 6, it is preferable that the end portion of each suction cup 150 forming part of the suction cup portion 101 is a pliable or soft portion. FIG. 8 is a front view as a schematic view showing the configuration of the suction cup portion 101 with the above-mentioned structure. In FIG. 8, since the pliable member 109 is provided at the end portion of the suction cup 150 of the suction cup portion 101, the end portion of the suction cup portion 101 is a pliable of flexible portion. The end portion of the suction cup portion 101 is softer than the inside of the suction cup portion 101. Thus, the trackability of the suction cup portion 101 to a pliable organ can be furthermore enhanced and the suction force can be improved. The pliable member 109 can be, for example, the material described above by referring to the first embodiment.

In the coronary artery bypass grafting device shown in FIG. 6, the connecting member 107 is provided between the suction cup portion 101 and the flexible tube 102, or between the suction cups 150 of the suction cup portion 101 so that they can be connected. The connecting member 107 allows the direction of one of the suction cup 150 and the flexible tube 102 to be variable to the direction of the other, and allows one of the suction cup portion 101 and the flexible tube 102 to be movable from the other. Likewise, the connecting member 107 may allow one of the two suction cups 150 of the suction cup portion 101 to be variable to the other, and allow one of the suction cups 150 of the suction cup portion 101 to be movable from the other. Since the posture of the flexible tube 102 is movable relative to the suction cup 150 in the suction cup portion 101, the torsion stress or the stress by the pulse of the heart can be absorbed when the flexible tube 102 is pulled in the direction different from the first connection direction, and the suction cup portion 101 can be prevented from being detached from the heart wall surface, thereby improving the safety. Additionally, since the posture of one of the suction cups 150 of the suction cup portion 101 is movable relative to the other, the trackability of the suction cup 150 during attachment can be furthermore improved not only on the substantially flat portion of the heart wall surface, but also on the curved surface. As the connecting member 107 for allowing the flexible tube 102 to be arbitrarily movable relative to the suction cup portion 101, or the connecting member 107 for allowing one of the suction cups 150 of the suction cup portion 101 to be movable relative to the other, for example, a bellows tube for communication with the suction cup 150 and the flexible tube 102 can be used.

The connecting member 107 may also be configured such that the angular movable range of the flexible tube 102 relative to the suction cup portion 101 on the plane parallel to the attachment surface of the suction cup portion 101, or the angular movable range of one of the suction cups 150 of the suction cup portion 101 relative to the other can be 30 degrees or more and 180 degrees or less. The connecting member 107 may also be configured such that the angular movable range of the flexible tube 102 relative to the suction cup portion 101, or the angular movable range of one of the suction cups 150 of the suction cup portion 101 relative to the other on the vertical plane perpendicular to the attachment surface of the suction cup portion 101 can be 30 degrees or more and 180 degrees or less. By setting the angular movable range as 30 degrees or more, the freedom of the movement of the flexible tube 102 relative to the suction cup portion 101, or the freedom of the movement of one of the suction cups 150 of the suction cup portion 101 relative to the other can be sufficiently ensured. By setting the angular movable range as 180° or less, the torsion in the heart wall surface attached to the suction cup portion 101 can be suppressed, thereby holding the heart with high accuracy.

Third Embodiment

In the coronary artery bypass grafting device according to the above-mentioned embodiments, an attachment member may further include an auxiliary member for use in arranging a suction cup portion at a predetermined position of an object to be attached. The case in which the coronary artery bypass grafting device according to the first embodiment is used is explained below by referring to FIG. 9 and FIG. 10.

Figure 9:
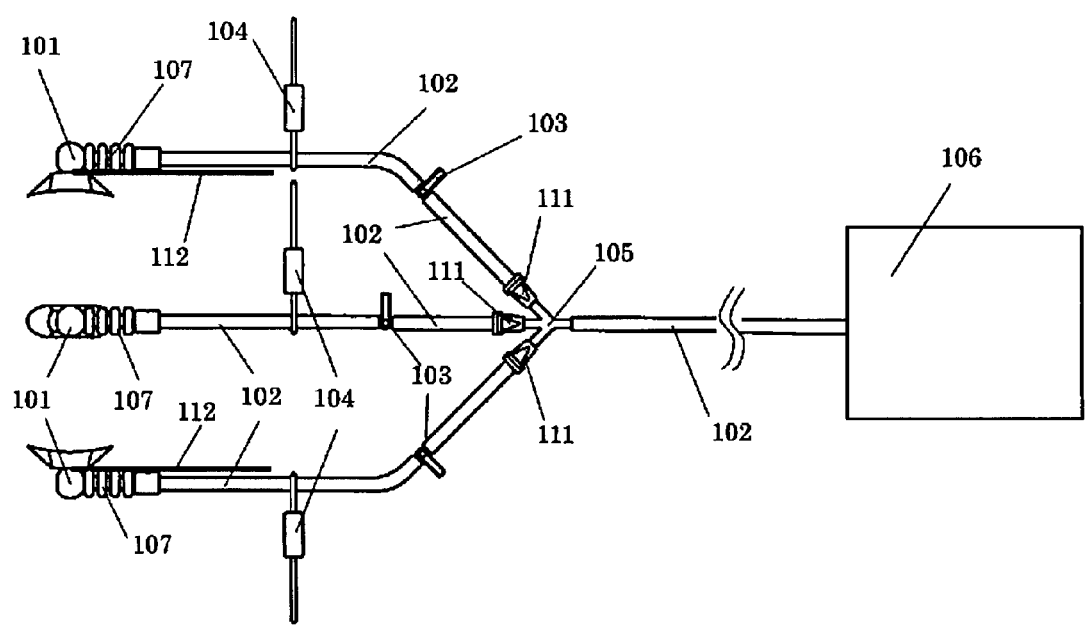
FIG. 9 is a drawing schematically showing a configuration of a coronary artery bypass grafting device related to an embodiment.
Figure 10:
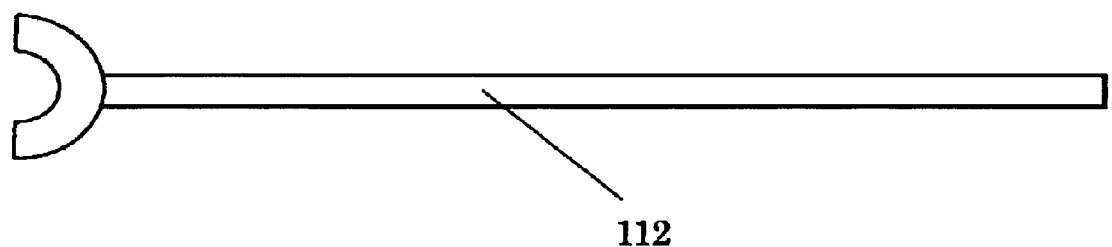
FIG. 10 is a drawing schematically showing a configuration of an insertion assisting member of a coronary artery bypass grafting device related to an embodiment.

FIG. 9 is a schematic view showing the configuration of the coronary artery bypass grafting device according to the present embodiment. FIG. 10 is a plan view of an example of the configuration of an insertion auxiliary member 112 of the coronary artery bypass grafting device shown in FIG. 9.

The coronary artery bypass grafting device shown in FIG. 9 is configured to further provide the insertion auxiliary member 112 for the coronary artery bypass grafting device shown in FIG. 1.

The insertion auxiliary member 112 is used in arranging the suction cup portion 101 at a predetermined position of the heart wall surface. The insertion auxiliary member 112 is configured to be removable from the suction cup portion 101. Practically, it includes a pole-shaped grasping unit and an engagement unit which is provided at the end portion of the grasping unit and is engaged as removable from the suction cup portion. An operator grasps the grasping unit directly or using a grasping member, arranges the suction cup portion 101 at a predetermined position of the heart wall surface, thereby attaching the suction cup portion 101 to the wall surface.

The shape of the tip portion of the insertion auxiliary member 112, that is, the shape of the plane of the engagement unit may be, for example, U-shaped. Thus, the U-shaped portion at the tip portion of the insertion auxiliary member 112 encloses the suction cup portion, and the insertion auxiliary member 112 is pushed into the U-shaped portion, thereby easily arranging the suction cup portion 101 in the heart wall surface. The insertion auxiliary member 112 can be curved into an arbitrary shape. Thus, the suction cup portion 101 can also be arranged on the heart wall portion on the back of the heart.

The pole-shaped portion is configured by a material having the hardness allowing the portion to be arbitrarily changed during operation. The material of the insertion auxiliary member 112 can be metal and the like, such as stainless-steel and the like. Thus, the hardness with which an operator can easily change the shape can be acquired with the hardness of the insertion auxiliary member 112 maintained. Therefore, the effect of the pushing the suction cup portion 101 using the insertion auxiliary member 112 can be improved.

The size of the insertion auxiliary member 112 can be, for example, 50 mm or more in total length, and 100 mm or more preferably. In the case of the above-mentioned U-shaped tip end portion, the outer diameter of the U-shaped portion can be, for example, 2 mm or more and 4 mm or less.

As shown in FIG. 9 and FIG. 10, in the present embodiment, the insertion auxiliary member 112 whose shape can be arbitrarily changed and which can be removable from the above-mentioned suction cup portion 101 of the coronary artery bypass grafting device is provided. Thus, as compared with the state in which the entire heart is exposed by the median sternotomy, the arrangement of the suction cup portion on the heart wall surface can be facilitated with the heart partially exposed by the costotome of a smaller scale by which the suction portion is difficult to be arranged on the heart wall surface.

Specifically, the insertion auxiliary member 112 is hung on the suction cup portion 101, and the insertion auxiliary member 112 is grasped and moved, thereby positioning the suction cup portion 101 at a predetermined position. Then, a suction pressure is applied to the suction cup portion 101, after the suction cup portion 101 is attached to the heart wall surface, the insertion auxiliary member 112 is pulled toward the operator, and thereby the insertion auxiliary member 112 can be separated from the suction cup portion 101 and removed. Thus, when the insertion auxiliary member 112 is provided, the insertion auxiliary member 112 is prevented from interrupting the operation using the insertion auxiliary member 112.

Fourth Embodiment

Figure 11:
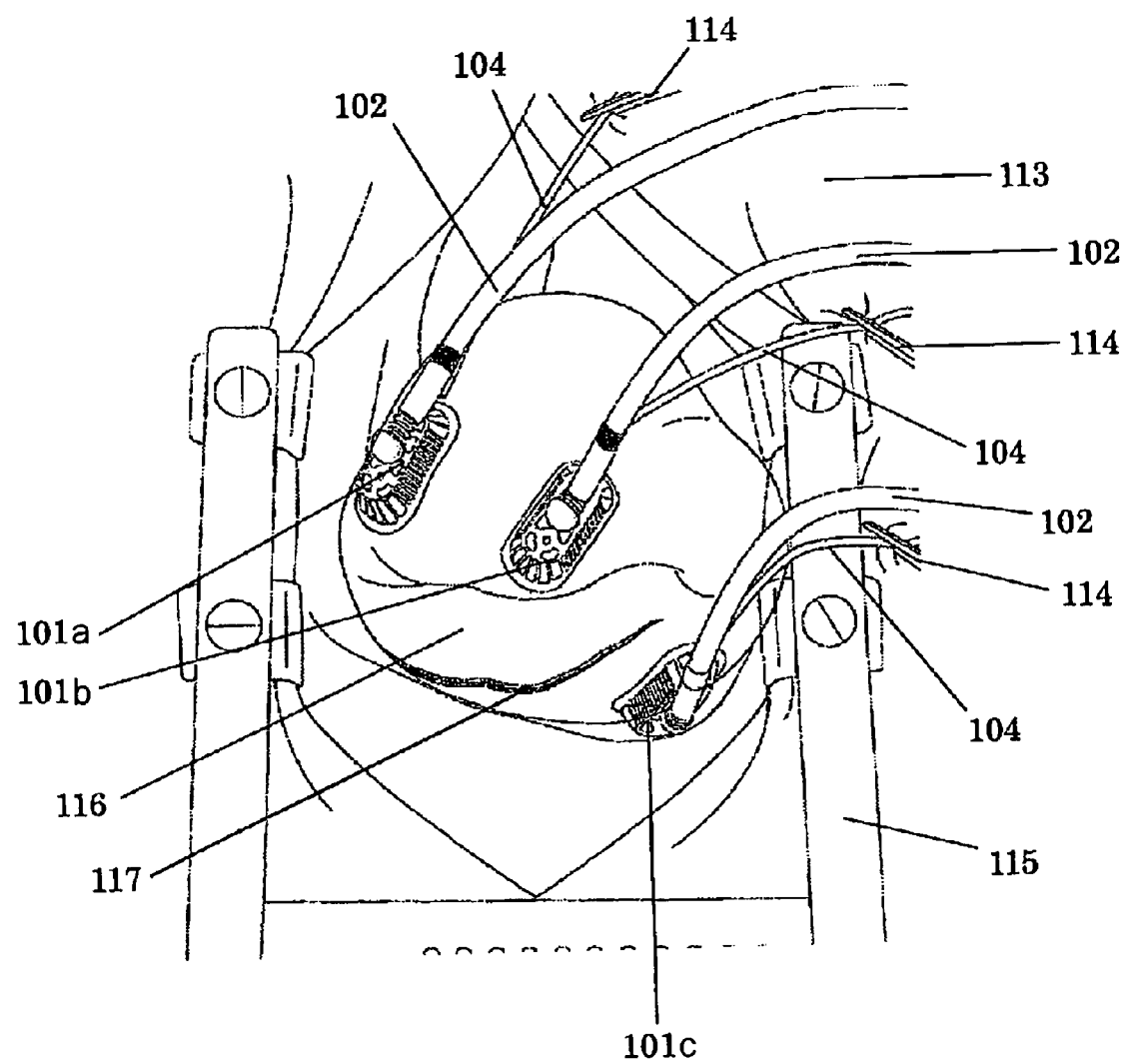
FIG. 11 is a drawing schematically showing a method of using a coronary artery bypass grafting device related to an embodiment.

The present embodiment relates to a method of performing a surgical therapy on a heart using a coronary artery bypass grafting device described in the above-mentioned embodiments. The case using the coronary artery bypass grafting device shown in FIG. 1 is explained by referring to FIG. 11. In the coronary artery bypass grafting device shown in FIG. 11, a first suction cup portion 101a, a second suction cup portion 101b, and a third suction cup portion 101c are provided as the suction cup portion 101. The tubular holding member 104 is arranged parallel to the flexible tube 102 of each attachment member. The holding member 104 is arranged at the suction source side 106 (not shown in the drawings) not beyond the communicating member 107, that is, closer to the base end side.

In the present embodiment, for example, the operation can be performed in the following procedure.

Step 101: When a heart is in the first position, a suction cup portion (first suction cup portion 101a) is arranged in a predetermined position of the heart wall surface.

Step 102: A suction pressure is applied to the first suction cup portion 101a, and the first suction cup portion 101a is attached to a predetermined position.

Step 103: Another suction cup portion (second suction cup portion 101b) is arranged in another position of the heart wall surface.

Step 104: Using the same suction source as the suction source (not shown in the drawings) from which the suction pressure is applied to the first suction cup portion 101a, the suction pressure is applied to the second suction cup portion 101b, and the second suction cup portion 101b is attached to another position.

Step 105: A further suction cup portion (third suction cup portion 101c) is arranged in a further position on the heart wall surface.

Step 106: Using the same suction source as the suction source (not shown in the drawings) from which the suction pressure is applied to the first suction cup portion 101a, the suction pressure is applied to the third suction cup portion 101c, and the third suction cup portion 101c is attached to a further position.

Step 107: The heart is held in the second position by drawing and holding: a holding member 104 for holding the flexible tube 102 for which the first suction cup portion 101a is provided; another holding member 104 for holding the flexible tube 102 for which the second suction cup portion 101b is provided; and a further holding member 104 for holding the flexible tube 102 for which the third suction cup portion 101c is provided.

Step 108: A surgical therapy is performed on the heart in the second position.

To be more concrete, with the heart completely exposed by the median sternotomy and placed in the first position, the first suction cup portion 101a and the second suction cup portion 101b are arranged at the peripheral portion of the heart wall surface, attached by the suction pressure of −300 mmHg, and the third suction cup portion 101c is arranged at the lower portion of the heart wall surface, and attached by the suction pressure of −300 mmHg. Then, each holding member 104 is drawn, the holding member 104 is fixed to the operation area drape 113 by the holder 114, and the heart is held in the second position. With the heart 116 in the second position, the coronary artery 117 as a target of a bypass anastomosis is exposed, and is drawn from three directions so that the heart cannot be deformed, therefore the pulsing heart can be stably held. Therefore, according to the present embodiment, the bypass anastomosis can be safely and surely performed. Although not shown in the drawings, the first suction cup portion 101a, the second suction cup portion 101b, and the third suction cup portion 101 care communicating with the same suction source.

In the explanation above, three suction cup portions 101 (the suction cup portion 101a to the suction cup portion 101c) are provided, but when two suction cup portions 101 are used, the heart is to be held in the second position by drawing and holding a holding member 104 for holding the flexible tube 102 provided with the first suction cup portion 101a and another holding member 104 for holding the flexible tube 102 provided with the second suction cup portion 101b in step 107 after step 101 to step 104 above, and then the process in step 108 is to be performed.

Described above are the embodiments according to the present invention. These embodiments are exemplified only, and those skilled in the art understand that there are many other variations that are within the scope of the present invention. Furthermore, the present invention is not limited to the coronary artery bypass grafting device not for a heart, but also can be applied to other organs, which is well understood by those skilled in the art.

For example, the above-mentioned coronary artery bypass grafting device is configured as having three suction cup portions 101 connected to the suction source 106, but the number of suction cup portions 101 are three or more, that is, four suction cup portions may also be used.

It is also possible to provide a trap between the above-mentioned coronary artery bypass grafting device and the suction source 106 to trap blood, body fluid, lavage fluid and the like.

The above-mentioned coronary artery bypass grafting device can be not only used as a treatment tool for a heart of a person but also used as a treatment tool for a heart of other animals such as mammalia and the like.

The invention claimed is:

1. A coronary artery bypass grafting device comprising:
    a plurality of attachment members each including:
        a flexible tube;
        a suction cup portion, having a communication opening that communicates with said flexible tube, provided at a tip end side of said flexible tube;
        a switching member provided in said flexible tube; and
        a holding member that holds said flexible tube,
    a branch portion that communicates with each flexible tube of said plurality of attachment members; and
    a main tube that communicates with said branch portion for connecting with a suction unit, wherein
    at least one of said attachment members further includes a check valve provided in said flexible tube,
    said switching member switches between a state for bringing said communication opening into communication with said branch portion, and a state for interrupting communication between said communication opening and said branch portion, and
    said check valve circulates fluid from said communication opening side to said branch portion side in only one direction.

2. The coronary artery bypass grafting device according to claim 1,
    wherein at least one of said attachment members further comprises an auxiliary member used for placing said suction cup portion in a predetermined position on a subject to be attached.

3. The coronary artery bypass grafting device according to claim 1,
    wherein said device comprises at least three attachment members.

4. The coronary artery bypass grafting device according to claim 1, wherein
    said check valve has a couple of valve bodies which are in contact with each other at tips of said valve bodies to be in a closed state, and
    said check valve is adapted to be opened when a base end side of said check valve is at a negative pressure with respect to said suction cup portion, and closed when the base end side of said check valve is at a relatively positive pressure with respect to said suction cup portion.

5. The coronary artery bypass grafting device according to claim 1,
    wherein said check valve is a duckbill valve.

6. The coronary artery bypass grafting device according to claim 1,
    wherein said check valve provided in said flexible tube provided with said suction cup portion is adapted to vibrate and generate a leak sound when the suction cup portion attached to the subject to be attached under a predetermined suction pressure is detached with said suction pressure being applied.

7. The coronary artery bypass grafting device according to claim 1,
    further comprising a connecting member that connects said suction cup portion and said flexible tube between said suction cup portion and said flexible tube, wherein said connecting member communicates with said suction cup portion and said flexible tube, and is adapted so that the orientation of one of said suction cup portion and said flexible tube is variable relative to the other.

8. The coronary artery bypass grafting device according to claim 7,
wherein said connecting member comprises a bellows tube communicating with said suction cup portion and said flexible tube.

9. The coronary artery bypass grafting device according to claim 8,
wherein an angular movable range of said flexible tube relative to said suction cup portion is not less than 30 degrees and not more than 180 degrees in a vertical plane perpendicular to the attachment surface of said suction cup portion.

10. The coronary artery bypass grafting device according to claim 7,
wherein an angular movable range of said flexible tube relative to said suction cup portion is not less than 30 degrees and not more than 180 degrees in a horizontal plane parallel to an attachment surface of said suction cup portion.

11. The coronary artery bypass grafting device according to claim 1,
wherein said suction cup portion further comprises:
a plurality of slit-like concaves extending from an end of said suction cup portion toward said communication opening.

12. The coronary artery bypass grafting device according to claim 1,
wherein the end portion of said suction cup portion is formed of a member softer than the inside of said suction cup portion.

13. The coronary artery bypass grafting device according to claim 1,
wherein said suction cup portions communicate with one suction unit via said flexible tube.

14. The coronary artery bypass grafting device according to claim 1,
wherein said check valve is arranged between said switching member and said branch portion in at least one of said attachment members.

15. The coronary artery bypass grafting device according to claims 1,
wherein said suction cup portion comprises a plurality of suction cups in at least one of said attachment members.

16. The coronary artery bypass grafting device according to claim 15,
wherein the shape of said suction cups is substantially circular.

17. A coronary artery bypass grafting device comprising:
a plurality of attachment members each having:
a flexible tube;
a suction cup portion, having a communication opening that communicates with said flexible tube, provided at a tip end side of said flexible tube;
a switching member provided in said flexible tube;
a holding member that holds said flexible tube; and
a check valve provided in said flexible tube
a branch portion that communicates with each flexible tube of said plurality of attachment members; and
a main tube that communicates with said branch portion for connecting with a suction unit, wherein
said switching member switches between a state for bringing said communication opening into communication with said branch portion, and a state for interrupting communication between said communication opening and said branch portion, and
said check valve circulates fluid from said communication opening side to said branch portion side in only one direction.

18. A method for surgically treating a heart using a coronary artery bypass grafting device comprising
a plurality of attachment members each including:
a flexible tube;
a suction cup portion, having a communication opening that communicates with said flexible tube, provided at a tip end side of said flexible tube;
a switching member provided in said flexible tube; and
a holding member that holds said flexible tube,
a branch portion that communicates with each flexible tube of said plurality of attachment members; and
a main tube that communicates with said branch portion for connecting with a suction unit, wherein
at least one of said attachment members further includes a check valve provided in said flexible tube,
said switching member switches between a state for bringing said communication opening into communication with said branch portion, and a state for interrupting communication between said communication opening and said branch portion, and
said check valve circulates fluid from said communication opening side to said branch portion side in only one direction;
wherein the method comprises attaching said suction cup portion to a heart wall surface while applying a suction pressure to said suction cup portion of said plurality of attachment members by sucking said main tube using said suction unit, in a state that said switching member brings said communication opening into communication with said branch portion; and surgically treating said heart.

19. The method according to claim 18,
wherein attaching said suction cup portion to said heart wall surface includes:
placing a first suction cup portion in a predetermined position on said heart wall surface when the heart is in a first position;
applying a suction pressure to said first suction cup portion by said suction unit and attaching said first suction cup portion to said predetermined position;
placing a second suction cup portion in a second position on said heart wall surface;
applying a suction pressure to said second suction cup portion by said suction unit and attaching said second suction cup portion to said second position and;
pulling and holding a first holding member that holds a flexible tube provided with said first suction cup portion and a second holding member that holds a flexible tube provided with said second suction cup portion to hold the heart in a second position;
wherein, said heart is surgically treated while in said second position.

20. The method according to claim 19,
wherein at least one of said attachment members further comprises an auxiliary member used for placing said suction cup portion in a predetermined position on a subject to be attached,
and placing said first suction cup portion in the predetermined position on the heart wall surface comprises placing said first suction cup portion in said predetermined position with said auxiliary member.

21. The method according to claim 18,
wherein attaching said suction cup portion to said heart wall surface includes:
placing a first suction cup portion in a predetermined position on said heart wall surface when the heart is in a first position;
applying a suction pressure to said first suction cup portion by said suction unit and attaching said first suction cup portion to said predetermined position;
placing a second suction cup portion in a second position on said heart wall surface;
applying a suction pressure to said second suction cup portion by said suction unit and attaching said second suction cup portion to said second position;
placing a third suction cup portion in a third position on said heart wall surface;
applying a suction pressure to said third suction cup portion by said suction unit and attaching said third suction cup portion to said third position; and
pulling and holding a first holding member that holds a flexible tube provided with said first suction cup portion, a second holding member that holds a flexible tube provided with said second suction cup portion, and a third holding member that holds a flexible tube provided with said third suction cup portion to hold the heart in a second position;
wherein, said heart is surgically treated while in said second position.

22. The method according to claim 21,
wherein at least one of said attachment members further comprises an auxiliary member used for placing said suction cup portion in a predetermined position on a subject to be attached, and placing said first suction cup portion in the predetermined position on the heart wall surface comprises placing said first suction cup portion in said predetermined position with said auxiliary member.

* * * * *